US008321158B2

(12) United States Patent
Proefke et al.

(10) Patent No.: US 8,321,158 B2
(45) Date of Patent: Nov. 27, 2012

(54) METHOD AND SYSTEM FOR MONITORING FRESHNESS OF FUEL IN VEHICLES

(75) Inventors: David T. Proefke, Madison Heights, MI (US); Clark E. McCall, Ann Arbor, MI (US); William A. Biondo, Beverly Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 507 days.

(21) Appl. No.: 12/418,288

(22) Filed: Apr. 3, 2009

(65) Prior Publication Data
US 2010/0256931 A1    Oct. 7, 2010

(51) Int. Cl.
*G01F 23/00* (2006.01)
*G06F 17/40* (2006.01)
(52) U.S. Cl. .......................... 702/50; 702/183; 702/187
(58) Field of Classification Search .................... 702/50, 702/55, 176–173; 137/3, 87.02; 701/102
See application file for complete search history.

(56) References Cited

U.S. PATENT DOCUMENTS

| 5,216,409 | A  | * | 6/1993  | Ament et al. ................. 340/438 |
| 6,644,285 | B2 | * | 11/2003 | Bayerle et al. ................ 123/491 |
| 6,691,809 | B2 | * | 2/2004  | Hata et al. ................. 180/65.225 |
| 6,812,825 | B1 | * | 11/2004 | Volk ........................ 340/309.16 |
| 6,935,311 | B2 | * | 8/2005  | Visser et al. ............. 123/406.47 |
| 2004/0040619 | A1 | * | 3/2004  | Dehn et al. ..................... 141/110 |
| 2007/0101969 | A1 | * | 5/2007  | Lay et al. ....................... 123/304 |

OTHER PUBLICATIONS

Streva, E., Pereira, L., Sodré, J., and Pasa, V., "Gasoline-Ethanol Blend Aging Effects on Engine Performance and Exhaust Emissions," SAE Technical Paper 2003-01-3184, 2003, doi:10.4271/2003-01-3184.*
Wiki Answers—"Can you mix old gasoline with new gasoline," http://replay.waybackmachine.org/20080505030431/http://wiki.answers.com/Q/Can_you_mix_old_gasoline_with_new_gasoline.*
Unlogged T-Mac.*
Fuel Testers: Gas Expiration—Ethanol Blend Fuels Have a Short Shelf Life, Jun. 27, 2007, pp. 1-3, http://web.archive.org/web/20070627173036/http://www.fuel-testers.com/expiration_of_ethanol_gas.html.*
Streva, E., Pereira, L., Sodr& J., and Pasa, V., "Gasoline-Ethanol Blend Aging Effects on Engine Performance and Exhaust Emissions," SAE Technical Paper 2003-01-3184, 2003, doi:I 0.4271/2003-01-3184.*
Fuel Testers: Gas Expiration—Ethanol Blend Fuels Have a Short Shelf Life, Jun. 27, 2007, pp. 1-3, http://web.archive.~rg/web/2~~7~627173~36/http://www.fue~testers.c~m/expirati~n of ethanol_gas.html.*

* cited by examiner

*Primary Examiner* — Sujoy Kundu
*Assistant Examiner* — Michael Dalbo
(74) *Attorney, Agent, or Firm* — Ingrassia Fisher & Lorenz, P.C.

(57) ABSTRACT

A method for monitoring fuel freshness in a vehicle includes the steps of determining a measure of time that the fuel has been in the vehicle and initiating a remedy if the measure of time is greater than a predetermined threshold.

20 Claims, 2 Drawing Sheets

METHOD AND SYSTEM FOR MONITORING FRESHNESS OF FUEL IN VEHICLES

TECHNICAL FIELD

The present invention generally relates to the field of vehicles and, more specifically, to methods and systems for monitoring freshness of fuel in vehicles, for example in hybrid electric vehicles.

BACKGROUND OF THE INVENTION

Certain vehicles today, such as hybrid electric vehicles, can be driven with or without the use of fuel, depending on the mode of the vehicle as it is being driven. For certain users, for example of hybrid electric vehicles, the users' typical commuting practices may allow them to operate the vehicle in electric modes of operation for extended periods of time without using fuel. Under such circumstances, fuel may be allowed to remain in the fuel tank of the vehicle for a period of time such that the fuel has a level of freshness that is less than optimal.

Accordingly, it is desirable to provide an improved method for monitoring freshness of fuel in vehicles, such as hybrid electric vehicles. It is also desirable to provide an improved program product for such monitoring of fuel freshness in vehicles. It is further desirable to provide an improved system for such monitoring of fuel freshness in vehicles. Furthermore, other desirable features and characteristics of the present invention will be apparent from the subsequent detailed description and the appended claims, taken in conjunction with the accompanying drawings and the foregoing technical field and background.

SUMMARY OF THE INVENTION

In accordance with an exemplary embodiment of the present invention, a method for monitoring fuel freshness in a vehicle is provided. The method comprises the steps of determining a measure of time that the fuel has been in the vehicle and initiating a remedy if the measure of time is greater than a predetermined threshold.

In accordance with another exemplary embodiment of the present invention, a program product for monitoring fuel freshness in a vehicle is provided. The program product comprises a program and a computer-readable signal bearing media. The program is configured to at least facilitate determining a measure of time that the fuel has been in the vehicle and initiating a remedy if the measure of time is greater than a predetermined threshold. The computer-readable signal bearing media bears the program.

In accordance with a further exemplary embodiment of the present invention, a system for monitoring fuel flow in a vehicle is provided. The system comprises a sensor and a processor. The sensor is configured to at least facilitate obtaining data used for calculating a measure of time that the fuel has been in the vehicle. The processor is coupled to the sensor, and is configured to at least facilitate determining the measure of time using the data, and initiating a remedy if the measure of time is greater than a predetermined threshold.

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description is merely exemplary in nature, and is not intended to limit the invention or the application and uses of the invention. Furthermore, there is no intention to be bound by any expressed or implied theory presented in the preceding technical field, background, brief summary or the following detailed description.

Figure 1:
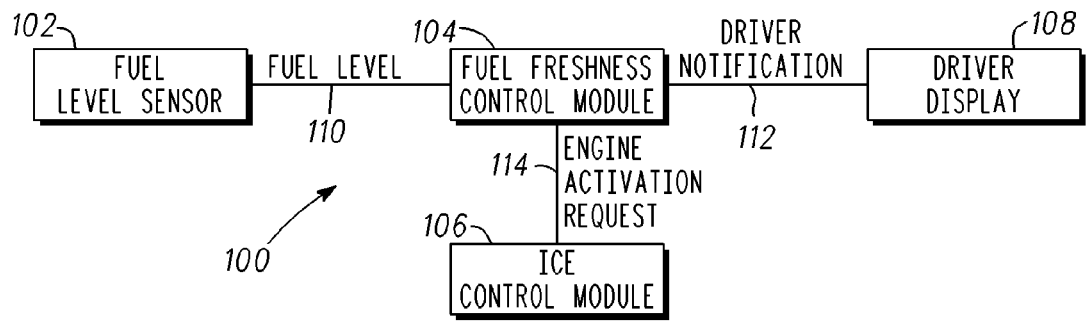
FIG. 1 is a functional block diagram of a monitoring and control system for monitoring and controlling freshness of fuel in a vehicle, in accordance with an exemplary embodiment of the present invention.

FIG. 1 is a functional block diagram of a monitoring and control system 100 for monitoring and controlling freshness of fuel in a vehicle, in accordance with an exemplary embodiment of the present invention. In a preferred embodiment, the vehicle comprises a hybrid electric vehicle. However, this may vary in other embodiments. In addition, in certain preferred embodiments, the vehicle comprises an automobile such as a sedan, a truck, a van, a sport utility vehicle, or another type of automobile. However, this may also vary in other embodiments. In various embodiments, the monitoring and control system 100 can be used in connection with any number of types of vehicles and/or systems thereof.

In the depicted embodiment, the monitoring and control system 100 comprises a fuel level sensor 102, a fuel freshness control module 104, an internal combustion engine (ICE) control module 106, and a driver display 108. In a preferred embodiment, the fuel level sensor 102 obtains values of fuel level 110 of a fuel tank of the vehicle at various points in time. The values of fuel level 110 are provided to the fuel freshness control module 104 for processing. In various other embodiments, other input data may be provided to the fuel freshness control module 104 by one or more other input units and/or sensors for processing by the fuel freshness control module 104.

The fuel freshness control module 104 monitors and controls fuel freshness in the vehicle. In so doing, the fuel freshness control module 104 utilizes the values of the fuel level 110 and/or other input data provided to the fuel freshness control module 104. Specifically, in a preferred embodiment, the fuel freshness control module 104 determines a weighted average measure of time that the fuel has been in the vehicle (also referenced herein as fuel age), using the values of the fuel level 110 and/or other input data and initiates a remedy (such as a driver notification 112 and/or an engine activation request, as depicted in FIG. 1 and described further below) if the measure of time (or fuel age) is greater than a predetermined threshold.

In so doing, the fuel freshness control module 104 performs the steps of one or more processes, such as the fuel freshness monitoring and control process 300 described further below in connection with FIG. 3, in accordance with an exemplary embodiment of the present invention. Also in a preferred embodiment, the fuel freshness control module 104 is part of a hybrid control module of an electric hybrid vehicle. However, this may vary in other embodiments. In addition, in a preferred embodiment, the fuel freshness control module 104 includes and/or is coupled to one or more computer systems, such as the computer system 200 described further below in connection with FIG. 2, that execute one or more program products and/or steps of the fuel freshness monitoring and control process 300 described further below in connection with FIG. 3.

As noted above, in one exemplary embodiment, the fuel freshness control module 104 provides a driver notification 112 as part of the above-mentioned remedy if the measure of time (or fuel age) is greater than the predetermined threshold. The driver notification 112 preferably includes a notification provided by the fuel freshness control module 104 via the driver display 108 informing the driver that the fuel in the vehicle's tank may not be at an optimal level of freshness. In addition, in certain embodiments, the driver notification 112 provides instructions for the driver to take one or more remedial actions, such as operating the vehicle in a fuel-burning mode using an internal combustion engine of the vehicle, adding fuel to the fuel tank, and/or adding a fuel additive to the fuel in the fuel tank.

In one exemplary embodiment, the driver display 108 comprises an audio display. In another exemplary embodiment, the driver display 108 comprises a video display. In yet other exemplary embodiments, the driver display 108 comprises both an audio display and a video display, and/or any one or more other different types of displays.

Also as noted above, in one exemplary embodiment, the fuel freshness control module 104 provides an engine activation request 114 as part of the above-mentioned remedy if the measure of time (or fuel age) is greater than the predetermined threshold. In certain embodiments, both a driver notification 112 and an engine activation request 114 may be provided, and/or one or more other remedies may be provided if the measure of time (or fuel age) is greater than the predetermined threshold.

The engine activation request 114 preferably includes a request by the fuel freshness control module 104 to the ICE control module 106 to operate an internal combustion engine of the vehicle in order to burn fuel. For example, in one preferred embodiment, the fuel freshness control module 104 commands the ICE control module 106, via the engine activation request 114, to operate an internal combustion engine of the vehicle in order to burn fuel the next time that the vehicle is operated by a user. For example, in one such embodiment, the ICE control module 106 may automatically place the vehicle in a fuel-burning, internal combustion engine mode the next time that the vehicle is operated by the user. Also, in certain embodiments, the engine activation request 114 may include a command for the ICE control module 106 to add a fuel additive to the fuel in the fuel tank. In addition, in a preferred embodiment, the ICE control module 106 includes and/or is coupled to one or more computer systems, such as the computer system 200 described further below in connection with FIG. 2, that execute one or more program products and/or steps of the fuel freshness monitoring and control process 300 described further below in connection with FIG. 3.

Figure 2:
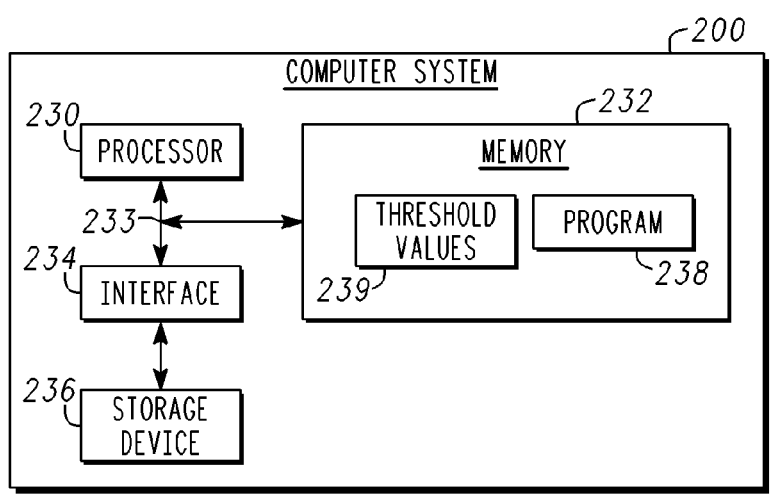
FIG. 2 is a function block diagram of a computer system that can be used in connection with the monitoring and control system of FIG. 1, for example in a control module thereof, in accordance with an exemplary embodiment of the present invention.

FIG. 2 is a function block diagram of a computer system 200 that can be used in connection with the monitoring and control system of FIG. 1, for example in the fuel freshness control module 104 and/or the ICE control module 106 thereof, in accordance with an exemplary embodiment of the present invention. For example, in one exemplary embodiment, the fuel freshness control module 104 and the ICE control module 106 utilize one or more common computer systems 200. In another exemplary embodiment, the fuel freshness control module 104 and the ICE control module 106 utilize one or more different computer systems 200.

As depicted in FIG. 2, the computer system 200 includes a processor 230, a memory 232, a bus 233, an interface 234, and a storage device 236 in an exemplary embodiment. The processor 230 performs the computation and control functions of the computer system 200 or portions thereof. Specifically, in a preferred embodiment, the processor 230 is configured to at least facilitate monitoring and/or controlling freshness of fuel in vehicles by implementing steps of one or more processes such as the fuel freshness monitoring and control process 300 of FIG. 3.

The processor 230 may comprise any type of processor or multiple processors, single integrated circuits such as a microprocessor, or any suitable number of integrated circuit devices and/or circuit boards working in cooperation to accomplish the functions of a processing unit. During operation, the processor 230 executes one or more programs 238 preferably stored within the memory 232 and, as such, controls the general operation of the computer system 200.

As referenced above, the memory 232 stores a program or programs 238 that execute one or more embodiments of processes such as the fuel freshness monitoring and control process 300 described below in connection with FIG. 3 and/or various steps thereof and/or other processes, such as those described elsewhere herein. In addition, in one preferred embodiment, the memory 232 stores one or more threshold values 239 for subsequent comparison with one or more data values in determining an amount of time in which the fuel has remained in the fuel tank and/or a freshness of the fuel in the fuel tank.

The memory 232 can be any type of suitable memory. This would include various types of dynamic random access memory (DRAM) such as SDRAM, various types of static RAM (SRAM), and various types of non-volatile memory (PROM, EPROM, and flash). It should be understood that the memory 232 may be a single type of memory component, or it may be composed of many different types of memory components. In addition, the memory 232 and the processor 230 may be distributed across several different computers. For example, a portion of the memory 232 may reside on a computer within a particular apparatus or processor, and another portion may reside on a remote computer.

The bus 233 serves to transmit programs, data, status, and other information or signals between the various components of the computer system 200. The bus 233 can be any suitable physical or logical means of connecting computer systems and components. This includes, but is not limited to, direct hard-wired connections, fiber optics, and infrared and wireless bus technologies.

The interface 234 allows communication to the computer system 200, for example from a vehicle user, a system operator, and/or another computer system, and can be implemented using any suitable method and apparatus. In a preferred embodiment, the interface 234 provides information to the processor 230 for use in monitoring and controlling the freshness of fuel in the vehicle.

The storage device 236 can be any suitable type of storage apparatus, including direct access storage devices such as hard disk drives, flash systems, floppy disk drives and optical disk drives. In one exemplary embodiment, the storage device 236 is a program product from which memory 232 can receive a program 238 that executes one or more embodiments of the fuel freshness monitoring and control process 300 of FIG. 3 and/or steps thereof as described in greater detail further below. In one preferred embodiment, such a program product can be implemented as part of, inserted into, or otherwise coupled to the monitoring and control system 100 of FIG. 1. As one exemplary implementation, the computer system 200 may also utilize an Internet website, for example for providing or maintaining data or performing operations thereon.

It will be appreciated that while this exemplary embodiment is described in the context of a fully functioning computer system for the computer system 200, those skilled in the art will recognize that the mechanisms of the present invention are capable of being distributed as a program product in a variety of forms, and that the present invention applies equally regardless of the particular type of computer-readable signal bearing media used to carry out the distribution. Examples of signal bearing media include: recordable media such as floppy disks, hard drives, memory cards and optical disks, and transmission media such as digital and analog communication links. It will similarly be appreciated that the computer system 200 depicted in FIG. 2 may comprise any one or more of a number of other types of control modules and/or computer systems in various other embodiments of the present invention. In addition, the fuel freshness control module 104 and/or the ICE control module 106 of FIG. 1 may be part of or coupled to one or more common or shared computer systems 200, one or more separate or different computer systems 200, and/or one or more other different types of computer systems and/or other systems and/or devices.

Figure 3:
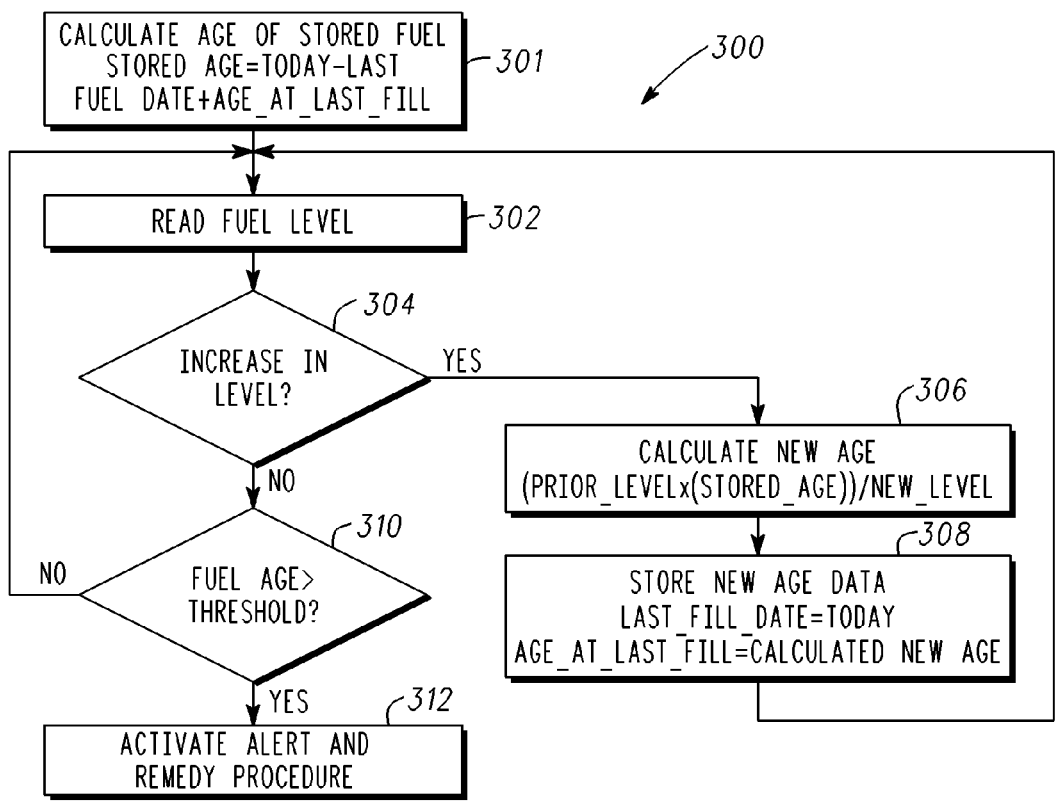
FIG. 3 is a flowchart of a fuel freshness monitoring and control process for monitoring and controlling freshness of fuel for a vehicle, and that can be implemented in connection with the monitoring and control system of FIG. 1 and the computer system of FIG. 2, in accordance with another exemplary embodiment of the present invention.

FIG. 3 is a flowchart of a fuel freshness monitoring and control process 300 for monitoring and controlling freshness of fuel for a vehicle, in accordance with an exemplary embodiment of the present invention. In a preferred embodiment, the fuel freshness monitoring and control process 300 can be implemented in connection with the monitoring and control system 100 of FIG. 1 and the computer system 200 of FIG. 2. However, it will be appreciated that in various embodiments the fuel freshness monitoring and control process 300 may also be implemented in connection with any number of different types of systems and/or other devices.

As depicted in FIG. 3, the fuel freshness monitoring and control process 300 includes the step of calculating the age of the stored fuel (step 301). The age of the stored fuel is calculated as follows:

Stored Fuel Age=(Age at Last Fill+(Today's Date−Last Fill Date)  (Equation 1), in which (i) Age at Last Fill represents the fuel age calculated at the time fuel has most recently been added to the fuel tank, (ii) Today's Date represents an actual calendar date as provided by other vehiclular data or an estimated date based on 24 hour increments since the time that fuel was last added to fuel tank, and (iii) the Last Fill Date represents a date in which fuel has most recently been added to the fuel tank. Also in a preferred embodiment, the stored fuel age is calculated by the fuel freshness control module 104 of FIG. 1, preferably by a processor thereof.

Process 300 also includes the step of reading a level of the fuel in a vehicle (step 302). During a first iteration of step 302, the fuel level is read or obtained at a first point in time. As will be detailed further below, in subsequent iterations of step 302, the fuel level is also read at subsequent points in time.

In a preferred embodiment, the fuel level read in each iteration of step 302 corresponds to the fuel level 110 of FIG. 1 of the fuel in a fuel tank of the vehicle at a particular point in time. Also in a preferred embodiment, at each such point in time the fuel level is read by a fuel level sensor 102 of FIG. 1 that is preferably disposed proximate the fuel tank of the vehicle.

A determination is then made as to whether there has been an increase in the fuel level (step 304). In a preferred embodiment, this determination refers to whether there has been an increase in the fuel level as determined between multiple iterations of step 302. Such a change in fuel level would occur when the driver or another individual partially or completely fills the fuel tank of the vehicle with fuel. Also in a preferred embodiment, this determination is made by the fuel freshness control module 104 of FIG. 1, preferably by a processor thereof.

If a determination is made that there has been an increase in the fuel level, then a current fuel age is calculated for the fuel in the fuel tank of the vehicle (step 306). As used herein in accordance with a preferred embodiment, fuel age represents an average amount of time that the fuel has remained in a fuel tank of the vehicle as measured at any particular point in time, such as a current point in time for the current fuel age. In a preferred embodiment, the current fuel age is calculated as follows:

Current Fuel Age=(Prior Level*(Stored Fuel Age))/New Fuel Level  (Equation 2), in which (i) the Prior Level represents a first fuel level of fuel in the vehicle's fuel tank as determined during a first iteration of step 302 at a first point in time before the most recent filling of the fuel tank, (ii) the Stored Fuel Age represents the age calculated in step 301; and (iii) the New Fuel Level is equal to a current fuel level of fuel in the vehicle's fuel tank as determined during a most recent iteration of step 302 at a second point in time. The second point in time preferably corresponds to the current point in time in which the current fuel age is calculated, or as close as possible thereto. However, the method of calculation may vary in other embodiments. Also in a preferred embodiment, the current fuel age is calculated by the fuel freshness control module 104 of FIG. 1, preferably by a processor thereof.

Current fuel age data is then stored (step 308) for use in subsequent determinations of fuel age (e.g., in steps 301 and 306). In a preferred embodiment, the current fuel age determined in step 306 is stored in a memory of the fuel freshness control module 104 of FIG. 1 for use in determining updated fuel ages in subsequent iterations. In addition, in a preferred embodiment, the new fuel level (or current fuel level) is also stored in a memory of the fuel freshness control module 104 of FIG. 1 as the new stored fuel level (or first fuel level) for use in determining updated fuel ages in subsequent iterations. Also in a preferred embodiment, the current date is similarly stored in a memory of the fuel freshness control module 104 of FIG. 1 as the new last fill date for use in determining updated fuel ages in subsequent iterations.

The process then returns to the above-referenced step 302, and the fuel level is read at a new, subsequent point in time. Steps 302-308 repeat through various iterations until a determination is made in an iteration of step 304 that there has been no increase in fuel level.

Once a determination is made in any iteration of step 304 that there has been no increase in fuel level, then a determination is made as to whether the current fuel age is greater than a predetermined threshold (step 310). In a preferred embodiment, the predetermined threshold represents a fuel age such that, if the average age of fuel in the vehicle exceeds the predetermined threshold, then this could result in less than desired operation of the vehicle in a fuel-burning mode. For example, in one exemplary embodiment, the predetermined threshold is six months. However, this may vary in other embodiments. Also in a preferred embodiment, this determination is made by the fuel freshness control module 104, preferably by a processor thereof by comparing the current fuel age with one or more threshold values stored in a memory thereof, such as the threshold values 239 stored in the memory 232 of FIG. 1.

If a determination is made that the current fuel age is greater than the predetermined threshold, then one or more remedies are initiated (step 312). Otherwise, the process returns to step 302 and steps 302-310 repeat until there is a determination in an iteration of step 310 that the current fuel age is greater than the predetermined threshold.

In a preferred embodiment, the one or more remedies initiated in step 312 include an alert or notification provided to the driver of the vehicle, such as the driver notification 112 described above in connection with FIG. 1. As discussed above, such a driver notification 112 may include, among other possible notifications, a notification that the fuel in the vehicle's tank may not be at an optimal level of freshness. Also as discussed above, such a driver notification 112 may include instructions for the driver to take one or more remedial actions, such as operating the vehicle in a fuel-burning mode using an internal combustion engine of the vehicle and/or adding a fuel additive to the fuel in the fuel tank.

In another preferred embodiment, the one or more remedies initiated in step 312 include an instruction for the ICE control module 106 of FIG. 6 to operate an internal combustion engine of the vehicle, such as the engine activation request 114 described above in connection with FIG. 1, and/or to provide a fuel additive to the fuel in the fuel tank. Also as discussed above, in certain embodiments both a driver notification and an engine activation request, and/or one or more other types of remedies, may be initiated in step 312 after it is determined in step 310 that the current fuel age is greater than the predetermined threshold.

Thus, the fuel freshness monitoring and control process 300 initiates appropriate remedial action once the fuel has remained in the fuel tank for an average amount of time that exceeds the predetermined threshold. The fuel freshness monitoring and control process 300 thereby helps to ensure, in a preferred embodiment, that the fuel in the vehicle's fuel tank is maintained at least at a baseline level of freshness, in order to maintain optimal performance even in situations in which the driver may not otherwise have operated the vehicle in a fuel-burning mode for an extended period of time.

It will be appreciated that various steps of the fuel freshness monitoring and control process 300 may vary from those depicted in FIG. 3 and/or described herein. It will similarly be appreciated that various steps of the fuel freshness monitoring and control process 300 may occur simultaneously with one another and/or in an order that differs from that depicted in FIG. 3 and/or described herein.

Accordingly, improved methods, program products, and systems are provided for monitoring and controlling fuel freshness in vehicles, for example in electric hybrid vehicles. The improved methods, program products, and systems allow for improved maintenance of fuel freshness in vehicles, such as electric hybrid vehicles, for example in situations in which the driver may not otherwise have operated the vehicle in a fuel-burning mode for an extended period of time. In such situations, the improved methods, program products, and systems initiate one or more remedies for freshening the fuel in the vehicle, such as by automatically operating an internal combustion engine of the vehicle or automatically adding a fuel additive to fuel in the vehicle's fuel tank, or by requesting that the driver operate the internal combustion engine of the vehicle or provide a fuel additive to the fuel in the fuel tank, and/or through one or more other notifications, actions, and/or other remedies.

It will be appreciated that, in various embodiments, the disclosed methods, program products, and systems may vary from those depicted in the figures and described herein. It will also be appreciated that, while the disclosed methods, program products, and systems are described above as being used in connection with a hybrid electric vehicle, this may also vary in other embodiments. It will similarly be appreciated that, while the disclosed methods, program products, and systems are described above as being used in connection with automobiles such as sedans, trucks, vans, and sports utility vehicles, the disclosed methods, program products, and systems may also used in connection with any number of different types of vehicles, and in connection with any number of different systems thereof and environments pertaining thereto.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method for monitoring freshness of fuel in a vehicle, the method comprising the steps of:
    determining, using a processor, a measure of time that the fuel has been in the vehicle, the measure of time comprising an average measure of time that the fuel from more than one fueling of the vehicle has remained on the vehicle; and
    initiating a remedy if the measure of time is greater than a predetermined threshold.

2. The method of claim 1, further comprising the steps of:
    determining a first level of the fuel at a first point in time; and
    determining a second level of the fuel at a second point in time;
    wherein the step of determining the measure of time comprises the step of determining the measure of time using the first level and the second level.

3. The method of claim 1, wherein the step of determining the measure of time comprises the steps of:
    determining a first point in time in which a first portion of the fuel was in the vehicle;
    determining a second point in time in which a second portion of the fuel was added to the vehicle; and
    determining the measure of time based at least in part on the determinations of the first and second points in time.

4. The method of claim 3, further comprising the steps of:
    determining an amount of the first portion of the fuel remaining in the vehicle when the second amount of fuel was added to the vehicle;
    determining a measure of an amount of the second portion of the fuel added to the vehicle; and
    determining the measure of time based also at least in part on the amount of the first portion of the fuel remaining in the vehicle when the second amount of fuel was added to the vehicle and the measure of an amount of the second portion of the fuel added to the vehicle.

5. The method of claim 1, wherein the step of initiating the remedy comprises the step of:
running an internal combustion engine of the vehicle if the measure of time is greater than a predetermined threshold.

6. The method of claim 1, wherein the step of initiating the remedy comprises the step of:
inserting an additive to the fuel if the measure of time is greater than a predetermined threshold.

7. The method of claim 1, wherein the step of initiating the remedy comprises the step of:
providing a notification to a driver of the vehicle if the measure of time is greater than a predetermined threshold.

8. A program product for monitoring freshness of fuel in a vehicle, the program product comprising:
a non-transitory computer readable medium containing computer instructions stored therein for causing a computer processor to perform:
determining a measure of time that the fuel has been in the vehicle, the measure of time comprising an average measure of time that the fuel from more than one fueling of the vehicle has remained in the vehicle; and
initiating a remedy if the measure of time is greater than a predetermined threshold.

9. The program product of claim 8, wherein the program is further configured to at least facilitate:
determining a first level of the fuel at a first point in time;
determining a second level of the fuel at a second point in time; and
determining the measure of time using the first level and the second level.

10. The program product of claim 8, wherein the program is further configured to at least facilitate:
determining a first point in time in which a first portion of the fuel was in the vehicle;
determining a second point in time in which a second portion of the fuel was added to the vehicle; and
determining the measure of time based at least in part on the determinations of the first and second points in time.

11. The program product of claim 10, wherein the program is further configured to at least facilitate:
determining an amount of the first portion of the fuel remaining in the vehicle when the second amount of fuel was added to the vehicle;
determining a measure of an amount of the second portion of the fuel added to the vehicle; and
determining the measure of time based also at least in part on the amount of the first portion of the fuel remaining in the vehicle when the second amount of fuel was added to the vehicle and the measure of an amount of the second portion of the fuel added to the vehicle.

12. The program product of claim 8, wherein the program is further configured to at least facilitate:
running an internal combustion engine of the vehicle if the measure of time is greater than a predetermined threshold.

13. The program product of claim 8, wherein the program is further configured to at least facilitate:
inserting an additive to the fuel if the measure of time is greater than a predetermined threshold.

14. The program product of claim 8, wherein the program is further configured to at least facilitate:
providing a notification to a driver of the vehicle if the measure of time is greater than a predetermined threshold.

15. A system for monitoring freshness of fuel in a vehicle, the program product comprising:
a sensor configured to at least facilitate obtaining data used for calculating a measure of time that the fuel has been in the vehicle the measure of time comprising an average measure of time that the fuel from more than one fueling of the vehicle has remained in the vehicle; and
a processor coupled to the sensor and configured to at least facilitate:
determining the measure of time using the data; and
initiating a remedy if the measure of time is greater than a predetermined threshold.

16. The system of claim 15, wherein the processor is further configured to at least facilitate:
determining a first level of the fuel at a first point in time;
determining a second level of the fuel at a second point in time; and
determining the measure of time using the first level and the second level.

17. The system of claim 15, wherein the processor is further configured to at least facilitate:
determining a first point in time in which a first portion of the fuel was in the vehicle;
determining a second point in time in which a second portion of the fuel was added to the vehicle; and
determining the measure of time based at least in part on the determinations of the first and second points in time.

18. The system of claim 17, wherein the processor is further configured to at least facilitate:
determining an amount of the first portion of the fuel remaining in the vehicle when the second amount of fuel was added to the vehicle;
determining a measure of an amount of the second portion of the fuel added to the vehicle; and
determining the measure of time based also at least in part on the amount of the first portion of the fuel remaining in the vehicle when the second amount of fuel was added to the vehicle and the measure of an amount of the second portion of the fuel added to the vehicle.

19. The system of claim 15, further comprising:
an internal combustion module coupled to the processor and configured to at least facilitate initiating the remedy by running an internal combustion engine of the vehicle if the measure of time is greater than a predetermined threshold.

20. The system of claim 15, further comprising:
a display coupled to the processor and configured to at least facilitate initiating the remedy by displaying a notification for a driver of the vehicle if the measure of time is greater than a predetermined threshold.

* * * * *